United States Patent [19]

Davis et al.

[11] Patent Number: 4,591,586
[45] Date of Patent: May 27, 1986

[54] 6-FLUORO-3-[3-(1-HETEROCYCLO)-PROPYL]-1,2-BENZISOXAZOLES FOR TREATMENT OF PAIN, HYPERTENSION AND PSYCHOSES

[75] Inventors: Larry Davis, Sergeantsville; Joseph T. Klein, Somerville, both of N.J.

[73] Assignee: Hoechst-Roussel Pharmaceuticals, Somerville, N.J.

[21] Appl. No.: 602,791

[22] Filed: Apr. 23, 1984

Related U.S. Application Data

[62] Division of Ser. No. 366,245, Apr. 9, 1982, Pat. No. 4,458,075.

[51] Int. Cl.$^4$ ............... A61K 31/55; A61K 31/42
[52] U.S. Cl. ............... 514/211; 514/212; 514/213; 514/227; 514/307; 514/321; 514/338; 514/374; 514/379
[58] Field of Search ............... 424/267, 272, 248.4, 424/258, 263; 514/374, 379, 321, 307, 338, 227, 211, 213, 212

[56] References Cited

FOREIGN PATENT DOCUMENTS 51-136666 11/1976 Japan ............... 546/198

OTHER PUBLICATIONS

Eadie, M., et al., *Anticonvulsant Therapy*, Churchill Livingstone, Edinburgh 1974, Index p. 1.
Woodbury, D., et al., (editors), *Antiepileptic Drugs*, Raven Press, NY, 1972, p. 531.
Benakis, A., et al., *Anticonvulsant Drugs*, vol. I, Pergamon Press, Oxford, 1973, pp. 385–386.
Arvanitaki, A., et al., *Anticonvulsant Drugs*, vol. II, Pergamon Press, Oxford, 1973, pp. 639–640.
Lednicer, D. (editor), *Central Analgetics*, Wiley Interscience, NY, 1982, p. 215.
De Stevens, G. (editor), Analgetics, *Academic Press*, NY, 1965, pp. 462–463.
*Burger's Medicinal Chemistry*, Wolff, M. (editor), 4th ed., Part III, John Wiley, NY, 1981, Chapters 52 and 55.
Koe, B., in *Industrial Pharmacology–Neuroleptics*, Futura Pub. Co., Mt. Kisco, NY, 1974, pp. 131–172.
Gilman, A., et al., (editors), *The Pharmacological Basis of Therapeutics*, 6th ed., MacMillan, New York, 1980, p. 243.
Gordon, M., (editor), *Psychopharmacological Agents*, vol. 1, Academic Press, New York, 1964, p. 602.

*Primary Examiner*—Richard A. Schwartz
*Attorney, Agent, or Firm*—Raymond R. Wittekind

[57] ABSTRACT

Novel 6-fluoro-3-[3-(1-heterocyclo)propyl]-1,2-benzisoxazoles, processes for the preparation thereof, and methods of treating psychoses, alleviating pain and reducing blood pressure employing the compounds and compositions thereof are disclosed. 3-{3-[N-(1-Piperidino)]aminopropyl}-6-fluoro-1,2-benzisoxazole, processes for the preparation thereof, and methods of treating pyschoses and alleviating pain employing the compound and compositions thereof are also disclosed.

6 Claims, No Drawings

6-FLUORO-3-[3-(1-HETEROCYCLO)PROPYL]-1,2-BENZISOXAZOLES FOR TREATMENT OF PAIN, HYPERTENSION AND PSYCHOSES

This is a division of application Ser. No. 366,245, filed Apr. 9, 1982, now U.S. Pat. No. 4,458,075.

DESCRIPTION OF THE INVENTION

The present invention relates to novel 3-[3-(1-heterocyclo)propyl]-1,2-benzisoxazoles. More particularly, the present invention relates to 6-fluoro-3-[3-(1-heterocyclo)propyl]-1,2-benzisoxazoles of Formula 1.

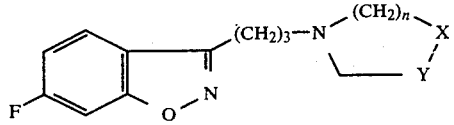

wherein X is O, C=O, a group of the formula

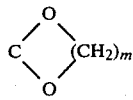

wherein m is 2 or 3, $CR_1R_2$ wherein $R_1$ is hydrogen, loweralkyl, phenyl or phenylloweralkyl and $R_2$ is hydrogen, cyano, loweralkylcarbonyl, phenylcarbonyl in which the phenyl group is substituted by halogen, or a group of the formula

wherein $R_3$ is loweralkyl, $CHZR_4$ wherein Z is O or S and $R_4$ is hydrogen or phenyl substituted by trifluoromethyl or one or two halogen groups, $CHNR_5R_6$ wherein $R_5$ is hydrogen or phenyl and $R_5$ is phenylcarbonyl or loweralkylcarbonyl, a group of the formula

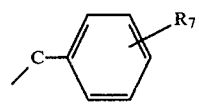

wherein $R_7$ is halogen; Y is $CH_2$; X and Y taken together form a phenyl nucleus and the dotted line represents an additional carbon to carbon bond when X is a group of the formula

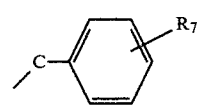

wherein $R_7$ is as above; n is 1, 2 or 3; the optical antipodes thereof or the pharmaceutically acceptable acid addition salts thereof, which are useful for treating psychoses, alleviating pain and reducing blood pressure, alone or in combination with inert psychoses treating, pain alleviating and blood pressure reducing adjuvents.

Subgeneric to the 6-fluoro-3-[3-(1-heterocyclo)propyl]-1,2-benzisoxazoles of formula 1 those wherein:

(a) X is $CR_1R_2$ wherein $R_1$ is hydrogen, loweralkyl, phenyl or phenylloweralkyl and $R_2$ is hydrogen, cyano, loweralkylcarbonyl, phenylcarbonyl in which the phenyl group is substituted by halogen, a group of the formula

wherein $R_3$ is loweralkyl, or a group of the formula

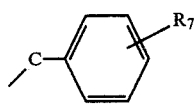

wherein $R_7$ is halogen; and n is 1, 2 or 3;

(b) X is $CR_1R_2$ wherein $R_1$ is hydrogen, loweralkyl, phenyl or phenylloweralkyl and $R_2$ is hydrogen; and n is 1, 2 or 3;

(c) X is $CHZR_4$ wherein Z is O or S and $R_4$ is hydrogen or phenyl substituted by trifluoromethyl or one or two halogen groups;

(d) X is C=O or a group of the formula

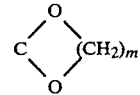

wherein m is 2 or 3;

(e) X is $CHNR_5R_6$ wherein $R_5$ is hydrogen or phenyl and $R_6$ is phenylcarbonyl or loweralkylcarbonyl;

(f) X is O; and (g) X and Y taken together form phenyl nucleus.

The present invention also relates to 3-{3-[N-(1-piperidino)]aminopropyl}-6-fluoro-1,2-benzisoxazole, processes for the preparation thereof, and method of treating psychoses and alleviating pain employing the compound and compositions thereof.

As used through the specification and appended claims, the term "alkyl" refers to a straight or branched chain hydrocarbon radical containing no unsaturation and having 1 to 7 carbon atoms such as methyl, ethyl, 1-propyl, 2-propyl, 1-butyl, 1-pentyl, 2-pentyl, 3-hexyl, 4-heptyl and the like; the term "halogen" refers to a member of a family consisting of chlorine, fluorine, bromine or iodine. The term "lower" as applied to any of the aforementioned groups refers to a group having a carbon skeleton containing up to and including 5 carbon atoms.

The compounds of the present invention which lack an element of symmetry exist as optical antipodes and as the racemic forms thereof. The optical antipode may be prepared from the corresponding racemic forms by standard optical resolution techniques, involving, for example, the separation of diastereomeric salts of those instant compounds characterized by the presence of a basic amino group and an optically active acid, or by the synthesis from optically active precursors.

The present invention comprehends all optical isomers and racemic forms thereof. The formulas of the compounds shown herein are intended to encompass all possible optical isomers of the compounds so depicted.

The novel 6-fluoro-3-{3-(1-heterocyclo)propyl]-1,2-benzisoxazoles of formula 1 wherein X is O, a group of the formula

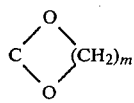

wherein m is 2 or 3, $CR_1R_2$ wherein $R_1$ is hydrogen, loweralkyl, phenyl or phenylloweralkyl and $R_2$ is hydrogen, cyano, loweralkylcarbonyl, phenylcarbonyl in which the phenyl group is substituted by halogen, $CHNR_5R_6$ wherein $R_5$ is hydrogen or phenyl and $R_6$ phenylcarbonyl or loweralkylcarbonyl; a group of the formula

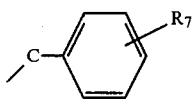

wherein $R_7$ is halogen; Y is $CH_2$; X and Y taken together form a phenyl nucleus and the dotted line represents an additional carbon to carbon bond when X is a group of the formula

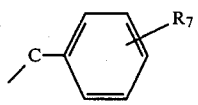

wherein $R_7$ is halogen; and n is 1, 2 or 3, are prepared by condensing 3-(3-chloropropyl)-6-fluoro-1,2-benzisoxazole of formula 2

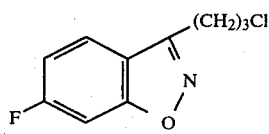

the synthesis of which is described in U.S. patent application Ser. No. 257,698, filed Apr. 27, 1981, with readily available heterocyclic amines of formula 3

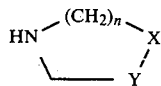

wherein X, Y and n are as immediately above. The condensation is conveniently performed by treating the halide 2 with the heterocyclic amine 3 in the presence of an acid acceptor, a displacement promoter and a suitable solvent. Among acid acceptors, there may be mentioned alkali metal carbonates and alkali metal bicarbonates such as, for example, lithium carbonate, sodium carbonate and potassium carbonate, and lithium bicarbonate, sodium bicarbonate and potassium bicarbonate. Potassium carbonate and sodium bicarbonate are preferred. Among displacement promoters, there may be mentioned alkali metal halides such as, for example, sodium iodide and potassium iodide, and sodium bromide and potassium bromide. Potassium iodide is preferred. Among suitable solvents, there may be mentioned polar aprotic substances such as, for example, dimethylformamide, dimethylacetamide and hexamethylphosphoramide. Dimethylformamide is preferred. The temperature at which the condensation is conducted is not narrowly critical. It is desirable, however to perform the condensation at a temperature within the range of about 50° C. to about 130° C. to assure a reasonable rate of conversion. A reaction temperature within the range of about 70° C. to 110° C. is preferred.

To prepare 3-[3-(1-heterocyclo)propyl]-1,2-benzisoxazoles of formula 1 wherein X is C=O or $CHZR_4$ wherein Z is O or S and $R_4$ is hydrogen or phenyl substituted by trifluoromethyl or one or two halogen groups; Y is $CH_2$; and n is 1, 2 or 3, a cyclic ketal of formula 1 wherein X is a group of the formula

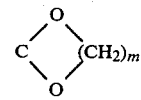

wherein m is 2 or 3; Y is $CH_2$; and n is 1, 2 or 3, is cleaved to a carbonyl compound of formula 1 wherein X is C=O; and Y and n are as above, which is reduced to a carbinol of formula 1 wherein X is $CHZR_4$ wherein Z is O; $R_4$ is hydrogen; and Y and n are as above, and then condensed with phenols of formula 4

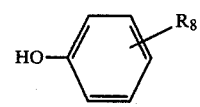

wherein $R_8$ is trifluoromethyl or one or two halogen groups to provide ethers of formula 1 wherein X is $CHZR_4$ wherein Z is O; $R_4$ is phenyl substituted by trifluoromethyl or one or two halogen groups and Y and n are as above, or treated with thiophthalimides of formula 5

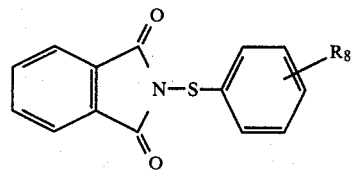

wherein $R_8$ is as above to provide thioethers of formula 1 wherein Z is S; $R_4$ is phenyl substituted by trifluoromethyl or one or two halogen groups and Y and n are as above.

The cyclic ketal cleavage is conveniently performed by conventional methods such as, for example, by contacting the ketal of formula 1 with hydrochloric acid in aqueous ethanol at moderate temperatures to furnish the carbonyl compound of formula 1.

The reduction is also conveniently performed by conventional methods such as, for example, by contacting the carbonyl compound of formula 1 with sodium borohydride in aqueous 2-propanol at ambient temperature to furnish the carbinol of formula 1.

Ether formation is accomplished by treating the carbinol of formula 1 with a phenol of formula 4 in an aromatic solvent such as benzene, toluene, xylene or the like, in the presence of a phosphine such as triethylphosphine, tri-n-butylphosphine, triphenylphosphine and the like, and a diloweralkyl azodicarboxylate such as dimethylazodicarboxylate, diethyl azodicarboxylate and the like. Benzene is the preferred aromatic solvent. Triphenylphosphine is the preferred phosphine and diethyl azodicarboxylate is the preferred diloweralkyl azodicarboxylate. The reaction temperature is not critical. However, to assure a reasonable rate of conversion, it is desirable to conduct it within the range of about −15° C. to 25° C., preferably at a temperature of about 5° to 10° C.

Thioether formation is effected by treating the carbinol of formula 1 with a thiophthalimide of formula 5 in an aromatic solvent such as benzene, toluene, xylene and the like in the presence of a phosphine such as triethylphosphine, tri-n-butylphosphine, triphenylphosphine and the like. Benzene is the preferred aromatic solvent and tri-n-butylphosphine is the preferred phosphine. Even though the temperature at which the reaction is conducted is not narrowly critical, it is desirable to perform it at a temperature within the range of about 0° to about 50° C. The preferred reaction temperature is about ambient temperature.

To prepare 3-[3-(1-heterocyclo)propyl]-1,2-benzisoxazoles of formula 1 wherein X is $CR_1R_2$ wherein $R_1$ is phenyl and $R_2$ is

wherein $R_3$ is loweralkyl; Y is $CH_2$; and n is 1, 2 or 3, a carbonyl compound of formula 1 wherein X is $CR_1R_2$ wherein $R_1$ is phenyl and $R_2$ is loweralkylcarbonyl; Y is $CH_2$; and n is 1, 2 or 3, is reduced with an alkali metal borohydride in an alkanol or mixture of alkanols at a temperature within the range of about 0° to 50° C. Among alkali metal borohydrides there may be mentioned lithium borohydride, sodium borohydride and potassium borohydride. Sodium borohydride is preferred. Among alkanols there may be mentioned methanol, ethanol, 1-propanol and 2-propanol. Among mixtures of alkanols there may be mentioned ethanol and 2-propanol and methanol and 2-propanol, a mixture of methanol and 2-propanol is preferred. A reduction temperature of about ambient temperature is also preferred.

The 6-fluoro-3-[3-(1-heterocyclo)propyl]-1,2-benzisoxazoles of the present invention are useful as analgesic agents due to their ability to alleviate pain in mammals which is demonstrated in the phenyl-para-quinone writhing assay in mice, a standard assay for analgesia [Proc. Soc. Exptl. Biol. Med., 95, 729 (1957)]. Presented in Table I is the analgesic effect of some of the compounds of the invention. expressed as the subcutaneous dose at which 50% of the phenyl-para-quinone induced writhing is inhibited in the animals, i.e., the $ED_{50}$ value and, as the percent decrease in writhing at a given dose.

TABLE 1

| Compound | Analgesic Activity $ED_{50}$ (mg/kg) |
|---|---|
| 1-[3-(6-Fluoro-1,2-benzisoxazol-3-yl)propyl]-4-phenylpiperidine hydrochloride | 1.0 |
| 1-[3-(6-Fluoro-1,2-benzisoxazol-3-yl)propyl] piperidine hydrochloride | 0.6 |
| 1-[3-(6-Fluoro-1,2-benzisoxazol-3-yl)propyl] pyrrolidine oxalate | 1.2 |
| 1-[3-(6-Fluoro-1,2-benzisoxazol-3-yl)propyl] morpholine oxalate | 2.2 |
| 1-[3-(6-Fluoro-1,2-benzisoxazol-3-yl)propyl]-2, | 1.3 |

TABLE 1-continued

| Compound | Analgesic Activity $ED_{50}$ (mg/kg) |
|---|---|
| 3,4,5,6,7-hexahydroazepine oxalate | |
| 4-Benzamido-1-[3-(6-fluoro-1,2-benzisoxazol-3-yl)propyl]-piperidine | 0.6 |
| 1-[3-(6-Fluoro-1,2-benzisoxazol-3-yl)propyl]-4-(N—propionylanilino)-piperidine hydrochloride | 4.0 |
| 1-[3-(6-Fluoro-1,2-benzixosazol-3-yl)propyl]-4-(4-fluorobenzoyl)-piperidine hydrochloride | 0.8 |
| 6-Fluoro-3-{3-[N—(1-piperidino)]-aminopropyl}-1,2-benzisoxazole oxalate | 5.0 |
| 8-[3-(6-Fluoro-1,2-benzisoxazol-3-yl)propyl]-1,4-dioxa-8-azaspiro[4,5]-decane hydrochloride | 1.4 |
| 1-[3-(6-Fluoro-1,2-benzisoxazol-3-yl)propyl]-4-phenylthiopiperidine-hydrochloride | 4.4 |
| 2-[3-(6-Fluoro-1,2-benzisoxazol-3-yl)propyl]-1,2,3,4-tetrahydroisoquinoline hydrochloride | 69% at 20 mg/kg |
| 1-[3-(6-Fluoro-1,2-benzisoxazol-3-yl)propyl]-4-hydroxypiperidine | 43% at 20 mg/kg |
| 1-[3-(6-Fluoro-1,2-benzisoxazol-3-yl)propyl]-4-(3,4-dichlorophenoxy)-piperidine hydrochloride | 49% at 20 mg/kg |
| 4-Acetyl-1-[3-(6-fluoro-1,2-benzisoxazol-3-yl)propyl]-4-phenylpiperidine hydrochloride | 46% at 20 mg/kg |
| propoxyphene | 3.9 |
| pentazocine | 1.3 |

Analgesia production is achieved when the present 6-fluoro-3-[3-(1-heterocyclo)propyl]-1,2benzisoxazoles are administered to a subject requiring such treatment as an effective oral, parenteral or intravenous dose of from 0.01 to 100 mg/kg of body weight per day. A particularly effective amount is about 10 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosage set forth herein are exemplary only and that they do not, to any extent, limit the scope or practice of the invention.

The 6-fluoro-3-[3-(1-heterocyclo)propyl]-1,2-benzisoxazoles of the present invention are also useful as antihypertensives due to their ability to reduce blood pressure in mammals. Antihypertensive activity is measured in the spontaneous hypertensive rat by the indirect tail cuff method described by A. Schwartz, Ed., "Methods in Pharmacology," Vol. 1, Appleton-Century-Crofts, New York, N.Y., 1971, page 135. According to this procedure, the test compound is administered orally to a group of 5 rats for 3 days in relation to a control group of the same number. The decrease in blood pressure is measured on the third day of administration. The antihypertensive activity expressed as the decrease in mean arterial blood pressure (mm of mercury) in this procedure of some of the compounds of the present invention is presented in Table II.

TABLE II

| Compound | Dose (mg/kg of Body wt) | Blood Pressure Decrease (mm/mercury) |
|---|---|---|
| 1-[3-(6-Fluoro-1,2-benzisoxazol-3-yl)propyl] piperidine hydrochloride | 50 | 30 |

TABLE II-continued

| Compound | Dose (mg/kg of Body wt) | Blood Pressure Decrease (mm/mercury) |
|---|---|---|
| 4-Benzamido-1-[3-(6-fluoro-1,2-benzisoxazol-3-yl)propyl]-piperidine | 50 | 44 |
| 1-[3-(6-Fluoro-1,2-benzisoxazol-3-yl)propyl]-4-(3-phenylpropyl)piperidine hydrochloride | 50 | 40 |
| 1-[3-(6-fluoro-1,2-benzisoxazol-3-yl)propyl]-4-methylpiperidine | 50 | 59 |
| 4-Benzyl-1-[3-(6-fluoro-1,2-benzisoxazol-3-yl)propyl]-piperidine hydrochloride | 50 | 71 |
| 4-(4-Chlorophenoxy)-1-[3-(6-fluoro-1,2-benzisoxazol-3-yl)propyl]-piperidine-hydrochloride | 50 | 39 |
| 1-[3-(6-Fluoro-1,2-benzisoxazol-3-yl)propyl]-4-(4-trifluoromethylphenoxy)-piperidine hydrochloride | 50 | 35 |
| guanethidine | 50 | 20 |

Blood pressure reduction is achieved when the present 6-fluoro-3-[3-(1-heterocyclo)propyl]-1,2-benzisoxazoles are administered to a subject requiring such treatment as an effective oral, parenteral or intravenous dose of from 0.01 to 50 mg/kg of body weight per day. A particularly preferred effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and they do not, to any extent, limit the scope or practice of the invention.

The 6-fluoro-3-[3-(1-heterocyclo)propyl]-1,2-benzisoxazoles of the present invention are useful for treating psychoses by virtue of their ability to block apomorphine-induce climbing in mammals.

Antipsychotic acitivity is determined in the climbing mice assay by a method similar to those described by P. Protais, et al., Psychopharmacol., 50, 1 (1976) and B. Costall, Eur. J. Pharmacol., 50, 39 (1978).

The subject CK-1 male mice (23-27 grams) are group-housed under standard laboratory conditions. The mice are individually placed in wire mesh stick cages (4"×4" by 10") and are allowed one hour for adaptation and exploration of the new environment. Then apomorphine is injected subcutaneously at 1.5 mg/kg, a dose causing climbing in all subjects for 30 minutes. Compounds to be tested for antipsychotic activity are injected intraperitoneally 30 minutes prior to the apomorphine challenge at a screening dose of 10 mg/kg.

For evaluation of climbing, 3 readings are taken at 10, 20 and 30 minutes after apomorphine administration according to the following scale:

| Climbing Behavior | Score |
|---|---|
| Mice With: | |
| 4 paws on bottom (no climbing) | 0 |
| 2 paws on the wall (rearing) | 1 |
| 4 paws on the wall (full climb) | 2 |

Mice consistently climbing before the injection of apormorphine will be discarded.

With full-developed apomorphine climbing, the animals are hanging onto the cage walls, rather motionless, over longer periods of time. By contrast, climbs due to mere motor stimulation usually only last a few seconds.

The climbing scores are individually totaled (maximal score: 6 per mouse over 3 readings) and the total score of the control group (vehicle intraperitoneally—apomorphine subcutaneously) is set to 100%. $ED_{50}$ values with 95% confidence limits are calculated by a Linear Regression Analysis. Antipsychotic activity expressed as the percentage decrease in climbing score or the estimated dose at which the animals experience at 50% decrease climbing scores of some of the instant 6-fluoro-3-[3-(1-heterocyclo)propyl]-1,2-benzisoxazoles as well as standard antipsychotics are presented in Table III.

TABLE III

| Compound | Dose (mg/kg of body wt) | Antipsychotic Activity (% decrease in climbing score) |
|---|---|---|
| 1-[3-(6-Fluoro-1,2-benzisoxazol-3-yl)propyl]-4-phenylpiperidine hydrochloride | 10 | 35 |
| 1-[3-(6-Fluoro-1,2-benzisoxazol-3-yl)propyl]-2,3,4,5,6,7-hexahydroazepine oxalate | 10 | 27 |
| 4-Benzamido-1-[3-(6-fluoro-1,2-benzisoxazol-3-yl)propyl]-piperidine | 10 | 49 |
| 1-[3-(6-Fluoro-1,2-benzisoxazol-3-yl)propyl]-4-(3-phenylpropyl)piperidine hydrochloride | 10 | 25 |
| 4-Benzyl-1-[3-(6-fluoro-1,2-benzisoxazol-3-yl)propyl]piperidine hydrochloride | 10 | 29 |
| 1-[3-(6-Fluoro-1,2-benzisoxazol-3-yl)propyl]-4-(4-fluorobenzoyl)piperidine hydrochloride | 3 | 91 |
| 6-Fluoro-3-{3-[N—(1-piperidino)]aminopropyl}-1,2-benzisoxazole oxalate | 10 | 36 |
| 1-[3-(6-Fluoro-1,2-benzisoxazol-3-yl)propyl]-4-phenylthiopiperidine hydrochloride | 10 | 27 |
| 1-[3-(6-Fluoro-1,2-benzisoxazol-3-yl)propyl]-4-(1-hydroxyethyl)-4-phenylpiperidine hydrochloride | 10 | 41 |
| 1-[3-(6-Fluoro-1,2-benzisoxazol-3-yl)propyl]-4-methylpiperidine | 7.6 | 50* |
| 8-[3-(6-Fluoro-1,2-benzisoxazol-3-yl)propyl]-1,4-dioxa-8-azaspiro[4.5]decane hydrochloride | 6.4 | 50* |
| 1-[3-(6-Fluoro-1,2-benzisoxazol-3-yl)propyl]-4-hydroxypiperidine | 10.4 | 50* |
| haloperidol (standard) | 0.11 | 50* |
| thioridazine (standard) | 3.5 | 50* |

*$ED_{50}$ - value

Antipsychotic activity is achieved when the present 6-fluoro-3-[3-(1-heterocyclo)propyl]-1,2-benzisoxazoles are administered to a subject requiring such treatment as an effective oral, parenteral or intravenous dose of from 0.01 to 50 mg/kg of body weight per day. A particularly preferred effective amount is about 5 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary and they do not, to any extent, limit the scope or practice of the invention.

Effective amounts of the compounds of the invention may be administered to a subject by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience or crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic caboxylic acids such as, for example, maleic acid, fumaric acid, oxalic acid and the like, and salts of tribasic cabocylic acids such as, for example, carboxysuccinic acid, citric acid and the like.

The active compounds of the present invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of present compound in such composition is such that a suitable dosage will be obtained. Preferred compositions and preparations according to the present invention are prepared so that an oral dosage unit form contains between 1.0-300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such a magnesium strearate or Sterotes; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of the aforesaid compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mgs of active compound.

The solutions or suspensions may also include the following components: a sterile diluent such as water for injection, saline solution, fixed oils, polyethylene glycols, glycerine, propylene glycol or other synthetic solvents; antibacterial, agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The following Examples are for illustrative purposes only and are not to be construed as limiting the invention.

EXAMPLE 1

1-[3-(6-Fluoro-1,2-benzisoxazol-3-yl)propyl]pyrrolidine oxalate

To 50 ml of dry dimethylformamide, was added 4.2 g of 3-(3-chloropropyl)-6-fluoro-1,2-benzisoxazole, 5.0 ml of pyrrolidine, 8.0 g of sodium bicarbonate, and a crystal of potassium iodide. After stirring at 70° C. for four hrs, the mixture was filtered and the filtrate was evaporated to an oil. The oil was stirred with 100 ml of water for five mins and then extracted with ether. The ether extract was washed with water (2x), saturated sodium chloride solution and dried over anhydrous magnesium sulfate. After filtering, the solvent was evaporated to an oil. The oil was treated with ethereal oxalic acid, and the resultant salt was recrystallized twice from ethyl acetate/methanol/ether to give 2.7 g, (44%) of product, mp 190°-200° C. (dec).

ANALYSIS: Calculated for $C_{14}H_{17}FN_2O \cdot (CO_2H)_2$: 56.80%C; 5.66%H; 8.28%N; Found: 56.38%C; 5.64%H; 8.34%N.

EXAMPLE 2

1-[3-(6-Fluoro-1,2-benzisoxazol-3-yl)propyl]piperidine hydrochloride

To 30 ml of dry dimethylformamide, was added 4.2 g of 3-(3-chloropropyl)-6-fluoro-1,2-benzisoxazole, 2.0 ml of piperidine, 8.0 g of sodium bicarbonate, and a crystal of potassium iodide. After stirring at 80° C. for two hrs, the mixture was filtered and the filtrate was evaporated to an oil. The oil was stirred with 100 ml of water for five mins and then extracted with ether. The ether extract was washed with water (2x), saturated sodium chloride solution and dried over anhydrous magnesium sulfate. After filtering, the solvent was evaporated to an oil. The oil was treated with ethereal hydrogen chloride, and the resultant salt was twice recrystallized from ethyl acetate/methanol/ether to give 2.5 g of (42%) product, mp 163°-165° C.

ANALYSIS: Calculated for $C_{15}H_{19}FN_2O \cdot HCl$: 60.29%C; 6.75%H; 9.38%N; Found: 60.03%C; 6.76%H; 9.24%N.

EXAMPLE 3

1-[3-(6-Fluoro-1,2-benzisoxazol-3-yl)propyl]-2,3,4,5,6,7-hexahydroazepine oxalate To 40 ml of dry dimethylformamide, was added 4.2 g of 3-(3-chloropropyl)-6-fluoro-1,2-benzisoxazole, 2.3 ml of hexamethyleneimine, 8.0 g of sodium bicarbonate, and a crystal of potassium iodide. After stirring at 80° C. for three hrs, the mixture was filtered and the filtrate was evaporated to an oil. The oil was stirred with 100 ml of water for five mins and then extracted with ether. The ether extract was washed with water (2x), saturated sodium chloride solution, and dried over anhydrous magnesium sulfate. After filtering, the solvent was evaporated to an oil. The oil was treated with ethereal hydrogen chloride, and the resultant salt was recrystallized twice from ethylacetate/methanol/ether to give 2.4 g (33%) of product, mp 141°–142° C. (dec).

ANALYSIS: Calculated for $C_{16}H_{21}FN_2O \cdot (CO_2H)_2$: 59.00%C; 6.33%H; 7.65%N; Found: 59.08%C; 6.40%H; 7.59%N.

EXAMPLE 4

1-[3-(6-Fluoro-1,2-benzisoxazol-3-yl)propyl]morpholine oxalate

To 35 ml of dry dimethylformamide, was added 4.2 g of 3-(3-chloropropyl)-6-fluoro-1,2-benzisoxazole, 3.0 ml of morpholine, 8.0 g of sodium bicarbonate, and a crystal of potassium iodide. After stirring at 90° C. for three hrs, the mixture was filtered and the filtrate was evaporated to an oil. The oil was stirred with 100 ml of water for five mins and then extracted with ether. The ether extract was washed with water (2x), saturated sodium chloride solution and dried over anhydrous magnesium sulfate. After filtering, the solvent was evaporated to an oil. The oil was treated with ethereal hydrogen chloride, and the resultant salt was recrystallized twice from ethyl acetate/methanol/ether to give the analytical sample, mp 178°–180° C. (dec).

ANALYSIS: Calculated for $C_{14}H_{17}FN_2O_2 \cdot (CO_2H)_2$: 54.23%C; 5.40%H; 7.91%N; Found: 53.89%C; 5.32%H; 7.96%N.

EXAMPLE 5

2-[3-(6-Fluoro-1,2-benzisoxazol-3-yl)propyl]-1,2,3,4-tetrahydroisoquinoline hydrochloride To 30 ml of dry dimethylformamide was added 2.13 g of 1,2,3,4-tetrahydroisoquinoline, 3.4 g of 3-(3-chloropropyl)-6-fluoro-1,2-benzisoxazole, 8.0 g of sodium bicarbonate, and a crystal of potassium iodide. After stirring at 100° C. for two hrs, the mixture was evaporated to an oil. The oil was stirred with 100 of ml water for five mins and then extracted with ether. The ether extract was washed with water (2x), saturated sodium chloride solution and dried over anhydrous magnesium sulfate. After filtering, the solvent was evaporated to an oil. A 4.5 g-portion of the oil was dissolved in ether and treated with ethereal hydrogen chloride, and the resultant salt was recrystallized from ethyl acetate/methanol/ether to give 3.0 g (54%) of product, mp 174°–176° C.

ANALYSIS: Calculated for $C_{19}H_{19}FN_2O \cdot HCl$: 65.79%C; 5.81%H; 8.08%N; Found: 65.93%C; 5.75%H; 8.00%N.

EXAMPLE 6

1-[3-(6-Fluoro-1,2-benzisoxazol-3-yl)propyl]-4-phenylpiperidine hydrochloride

To 30 ml of dry dimethylformamide was added 2.4 g of 4-phenylpiperidine, 3.4 g of 3-(3-chloropropyl)-6-fluoro-1,2-benzisoxazole, 8.0 g of sodium bicarbonate, and a few crystals of potassium iodide. After stirring at 100° C. for three hrs, the mixture was filtered and the filtrate was evaporated to an oil. The oil was stirred with 100 of ml water for five mins and then extracted into ether. The ether extract was washed with water (2x), saturated sodium chloride solution and dried over anhydrous magnesium sulfate. After filtering, the solvent was evaporated to an oil. The oil was dissolved in ether and treated with ethereal hydrogen chloride, and the resultant salt was twice recrystallized from ethyl acetate/methanol/ether to give 3.0 g (53%) of product, mp 213°–214° C.

ANALYSIS: Calculated for $C_{21}H_{23}FN_2O \cdot HCl$: 67.28%C; 6.45%H; 7.47%N; Found: 67.58%C; 6.54%H; 7.47%N.

EXAMPLE 7

1-[3-(6-Fluoro-1,2-benzisoxazol-3-yl)propyl]-4-(3-phenylpropyl)piperidine hydrochloride To 40 ml of dimethylformamide was added 4.06 g of 4-(3-phenylpropyl)piperidine, 3.4 g of 3-(3-chloropropyl)-6-fluoro-1,2-benzisoxazole, 10 g of milled potassium carbonate, and 0.01 g of potassium iodide. After stirring at 90° C. for three hrs, the mixture was cooled, filtered and the filtrate was evaporated to an oil. The oil was stirred with 100 ml of water for ten mins and then extracted with ether. The ether extract was washed with water (2x), saturated sodium chloride solution and dried over anhydrous magnesium sulfate. After filtering, the solution was acidified to pH 1 with ethereal hydrogen chloride. The resultant precipitate was collected and dried to give 5.0 g (60%) of product, mp 95° C. Recrystallization from ethyl acetate/methanol (5:1) gave the analytical sample, mp 136°–137° C.

ANALYSIS: Calculated for $C_{24}H_{29}FN_2O \cdot HCl$: 69.13%C; 7.25%H; 6.72%N; Found: 69.28%C; 7.25%H; 6.72%N.

EXAMPLE 8

4-Benzyl-1-[3-(6-fluoro-1,2-benzisoxazol-3-yl)propyl]-piperidine hydrochloride

A mixture of 5 g 3-(3-chloropropyl)-6-fluoro-1,2-benzisoxazole, 5 g of 4-benzylpiperidine, 10 g of potassium carbonate and a few crystals potassium iodide in 50 ml of dimethylformamide was stirred at 70° for 4.5 hr. The mixture was cooled, filtered and concentrated to an oil. The oil was stirred with water and extracted with ether. The organic extracts were washed with water (2x), saturated sodium chloride solution and dried over anhydrous magnesium sulfate, filtered and concentrated. The residue was treated with ethereal hydrogen chloride to give a salt. The salt was immediate rebasified to give an oil, which was purified by column chromatography (silica gel, tetrahydrofuran). The purified oil was treated with ethereal hydrogen chloride, and the resultant salt was recrystallized from ethyl acetate/methanol to give 2.8 g (31%) of product, mp 188°–189° C.

ANALYSIS: Calculated for $C_{22}H_{25}FN_2O.HCl$: 67.94%C; 6.74%H; 7.20%N; Found: 67.62%C; 6.78%H; 7.08%N.

EXAMPLE 9

4-Methyl-1-[3-(6-fluoro-1,2-benzisoxazol-3-yl)propyl]-piperidine hydrochloride A mixture of 5 g of 3-(3-chloropropyl)-6-fluoro-1,2-benzisoxazole, 2.9 g of 4-methylpiperidine, 10 g of potassium carbonate and a few crystals potassium iodide in 50 ml of dimethylformamide was stirred at 65°–70° C. for four hrs. The mixture was cooled, filtered and concentrated to an oil. The oil was stirred with water and extracted with ether. The organic extracts were washed with water (2x), saturated sodium chloride solution, dried over anhydrous magnesium sulfate, filtered and concentrated. The residue was treated with ethereal hydrogen chloride to give 4 g (55%) or product, mp 180°–182° C. Recrystallization from ethyl acetate/methanol gave the analytical sample, 189°–190° C.

ANALYSIS: Calculated for $C_{16}H_{21}FN_2O.HCl$: 61.43%C; 7.09 %H; 8.96%N; Found: 61.06%C; 7.02%H; 8.80%N.

EXAMPLE 10

4-(4-Chlorophenyl)-1-[3-(6-fluoro-1,2-benzisoxazol-3-yl)propyl]-1,2,3,6-tetrahydropyridine oxalate To 35 ml of dry dimethylformamide was added, 3.7 g of 4-(4-chlorophenyl)-1,2,3,6-tetrahydropyridine, 4.2 g of 3-(3-chloropropyl)-6-fluoro-1,2-benzisoxazole, 10 g of sodium bicarbonate, and a few crystals of potassium iodide. After stirring at 80° C. for one hr, the mixture was cooled, filtered and the filtrate was evaporated to an oil. The oil was stirred with 100 ml of water for five mins and then extracted with ether/ethyl acetate. The organic extract was washed with water (2x), saturated sodium chloride solution and dried over anhydrous magnesium sulfate. After filtering, the solvents were evaporated to an oil. The oil was dissolved in ether, filtered and treated with ethereal oxalic acid solution to give 5.2 g (56%) of product, mp 185° C. (dec). Two recrystallizations from ethyl acetate/methanol (9:1) gave the analytical sample, mp 207°–209° C. (dec).

ANALYSIS: Calculated for $C_{21}H_{20}ClFN_2O.(CO_2H)_2$: 59.93%C; 4.81%H; 6.08%N; Found: 60.11%C; 4.81%H; 5.97%N.

EXAMPLE 11

1-[3-(6-Fluoro-1,2-benzisoxazol-3-yl)propyl]-4-(N-propionylanilino)piperidine hydrochloride A mixture of 9.8 g of 3-(3-chloropropyl)-6-fluoro-1,2-benzisoxazole, 10 g of 4-(N-propionylanilino)piperidine, 7.1 g potassium carbonate, and a few crystals potassium iodide in 125 ml of dimethylformamide was stirred at 75° C. for three hrs. The reaction mixture was cooled, filtered and concentrated to an oil. The oil was stirred with water and extracted with ether. The organic extracts were washed with water (2x), saturated sodium chloride solution and dried over anhydrous magnesium sulfate, filtered and concentrated. The residue was treated with ethereal hydrogen chloride to give 10 g (55%) of product, mp 155°–160° C.

ANALYSIS: Calculated for $C_{24}H_{28}FN_3O_2.HCl$: 64.63%C; 6.55%H; 9.42%N; Found: 64.76%C; 6.53%H; 9.41%N.

EXAMPLE 12

4-Benzamido-1-[3-(6-fluoro-1,2-benzisoxazol-3-yl)propyl]-piperidine

A mixture of 3.7 g of 4-benzamidopiperidine, 4.3 g of 3-(3-chloropropyl)-6-fluoro-1,2-benzisoxazole, 8 g of sodium bicarbonate and a few crystals potassium iodide in 30 ml of dimethylformamide was stirred at 55° C. for 2.5 hrs. The reaction mixture was cooled and concentrated to an oil. The oil was stirred with water and extracted with ether/ethyl acetate. The organic extracts were washed with water, saturated sodium chloride solution, dried over anhydrous magnesium sulfate, filtered and concentrated. Crystallization of the residue with isopropyl ether gave 1.2 g (17%) of product, mp 150°–151° C.

ANALYSIS: Calculated for $C_{22}H_{24}FN_3O_2$: 69.27%C; 6.34%H; Found: 69.11%C; 6.35%H.

EXAMPLE 13

6-Fluoro-3-{3-[N-(1-piperidino)aminopropyl]-1,2-benzisoxazole oxalate

To 40 ml of dry dimethylformamide was added 4.2 g of 3-(3-chloropropyl)-6-fluoro-1,2-benzisoxazole, 3.0 g of N-aminopiperidine, 8.0 g of sodium bicarbonate, and a few crystals of potassium iodide. After stirring at 100° C. for two hrs, the mixture was evaporated. The residue was stirred with 100 ml of water for five mins and extracted into ether. The ether extract was washed with water (2x), saturated sodium chloride solution and dried over anhydrous magnesium sulfate and filtered. The filtrate was treated with ethereal oxalic acid, and the resultant salt was recrystallized from ethyl acetate/methanol/ether to give 2.8 g (38%) of product, mp 151°–153° C. Recrystallization from ethyl acetate/methanol/ether gave the analytical sample, mp 155°–157° C.

ANALYSIS: Calculated for $C_{15}H_{20}FN_3O.(CO_2H)_2$: 55.58%C; 6.04%H; 11.44%N; Found: 55.66%C; 5.98%H; 11.07%N.

EXAMPLE 14

8-[3-(6-Fluoro-1,2-benzisoxazol-3-yl)propyl]-1,4-dioxa-8-azaspiro[4,5]decane hydrochloride A mixture of 15 g of 1,4-dioxa-8-azaspiro-[4.5]-decane, 25 g of 3-(3-chloropropyl)-6-fluoro-1,2-benzisoxazole, 29 g of potassium carbonate and a few crystals potassium iodide in 80 ml of dimethylformamide was stirred at 70°–75° C. for two hrs. The mixture was cooled, filtered and concentrated to an oil. The oil was stirred with water and extracted with ether. The organic extracts were washed with water (2x), saturated sodium chloride solution, dried over anhydrous magnesium sulfate, filtered and concentrated. The residue was treated with ethereal hydrogen chloride to give 18 g (48%) or product, mp 170°–173° C. Recrystallization from ethyl acetate/methanol gave the analytical sample, mp 178°–179° C.

ANALYSIS: Calculated for $C_{17}H_{21}FN_2O_3.HCl$: 57.22%C; 6.21%H; 7.85%N; Found: 57.45%C; 6.13%H; 7.88%N.

EXAMPLE 15

1-[3-(6-Fluoro-1,2-benzisoxazol-3-yl)propyl]-4-piperidone

A mixture of 51 g of 8-[3-(6-fluoro-1,2-benzisoxazol-3-yl)propyl]-1,4-dioxa-8-azaspiro[4.5]decane hydrochloride, 100 ml of water, 100 ml of ethanol and 150 ml of 3N hydrochloric acid was heated at 75°–80° C. for 3 hrs and at ambient temperature overnight, with stirring. The mixture was cooled, basified with 3N sodium hydroxide solution and extracted with ethyl acetate-ether. The organic extracts were washed with water, saturated sodium chloride solution, dried over anhydrous magnesium sulfate and concentrated to give 37 g (96%) of product as an oil.

EXAMPLE 16

1-[3-(6-Fluoro-1,2-benzisoxazol-3-yl)propyl]-4-hydroxypiperidine

A solution of 5 g of 1-[3-(6-fluoro-1,2-benzisoxazol-3-yl)propyl]-4-piperidone and 1.4 g of sodium borohydride in 50 ml of isopropanol was stirred at ambient temperature for twenty hrs. The reaction mixture was quenched with methanol and concentrated. The residue was stirred with water and extracted with ether. The organic extracts were washed with water (2x), saturated sodium chloride solution, dried over anhydrous magnesium sulfate, filtered and concentrated to give 4.5 g (90%) of product. Recrystallization from ether gave the analytical sample, mp 88°–89° C.

ANALYSIS: Calculated for $C_{15}H_{19}FN_2O$: 64.73%C; 6.88%H; Found: 64.60%C; 6.95%H.

EXAMPLE 17

1-[3-(6-Fluoro-1,2-benzisoxazol-3-yl)propyl]-4-(3,4-dichlorophenoxy)piperidine hydrochloride To a solution of 6.4 g of 1-[3-(6-fluoro-1,2-benzisoxazol-3-yl)propyl]-4-hydroxypiperidine, 3.7 g of 3,4-dichlorophenol and 6.6 g of triphenylphosphine in 200 ml of benzene, cooled with an ice bath, was slowly added over one hr a solution of 4.4 g of diethyl azodicarboxylate in 50 ml of benzene. After stirring twenty hrs at ambient temperature, the reaction mixture was filtered and the filtrate was concentrated. The residue was treated with ethereal hydrogen chloride to yield a salt. The salt was rebasified to give an oil, which was purified by column chromatography (silica gel, tetrahydrofuran). The purified oil was treated with ethereal hydrogen chloride, and the resultant salt was recrystallized from ethyl acetate/methanol to give 2.4 g (23%) or product, mp 212°–214° C.

ANALYSIS: Calculated for $C_{21}H_{21}Cl_2FN_2O_2.HCl$: 54.86%C; 4.82%H; Found: 54.71%C; 4.82%H.

EXAMPLE 18

1-[3-(6-Fluoro-1,2-benzisoxazol-3-yl)propyl]-4-(4-trifluoromethylphenoxy)piperidine hydrochloride To a solution of 7.7 g of 1-[3-(6-fluoro-1,2-benzisoxazol-3-yl)propyl]-4-hydroxypiperidine, 4.5 g of α,α,α-trifluoromethyl-p-cresol and 8 g of triphenylphosphine in 200 ml of benzene, cooled with an ice-bath, was slowly added over one hour a solution of 5.3 g of diethyl azodicarboxylate in 50 ml of benzene. After stirring twenty hrs at ambient temperature, the reaction mixture was filtered and concentrated to an oil. The oil was treated with ethereal hydrogen chloride and the resultant solid was immediately recrystallized from ethyl acetate/methanol to give 2.5 g (20%) of product, mp 224°–225° C.

ANALYSIS: Calculated for $C_{22}H_{22}F_4N_2O_2.HCl$: 57.58%C; 5.05%H; Found: 57.49%C; 5.07%H.

EXAMPLE 19

4-(4-Chlorophenoxy)-1-[3-(6-fluoro-1,2-benzisoxazol-3-yl)propyl]-piperidine hydrochloride To a solution of 9.5 g of 1-[3-(6-fluoro-1,2-benzisoxazol-3-yl)-propyl]-4-hydroxypiperidine, 4.5 g of 4-chlorophenol and 9.8 g triphenylphosphine in 250 ml of benzene, cooled with an ice-bath, was slowly added over one hour a solution of 6.4 g of diethyl azodicarboxylate in 60 ml of benzene. After stirring one hr at ambient temperature, the reaction mixture was filtered and then concentrated to an oil. The oil was treated with ethereal hydrogen chloride to give 4.6 g (32%) of product, mp 209°–211° C. Recrystallization from ethyl acetate/methanol gave the analytical sample, mp 212°–213° C. (dec).

ANALYSIS: Calculated for $C_{21}H_{22}ClFN_2O_2.HCl$: 59.30%C; 5.45%H; Found: 59.17%C; 5.46%H.

EXAMPLE 20

1-[3-(6-Fluoro-1,2-benzisoxazol-3-yl)propyl]-4-phenylthiopiperidine hydrochloride To a suspension of 7 g of N-phenylthiophthalimide in 75 ml of benzene at 23° C., was added 5.6 g of tri-n-butylphosphine. The pot temperature rose to 29° C. After the temperature had fallen by 23° C., a solution of 6.7 g of 1-[3-(6-fluoro-1,2-benzisoxazol-3-yl)propyl]-4-hydroxypiperidine in 20 ml of benzene was slowly added. After the addition was complete, the reaction mixture was stirred twenty hrs at ambient temperature. The reaction mixture was filtered and concentrated. The residue was treated with ethereal hydrogen chloride. The resultant salt was immediately basified to give an oil. The oil was purified by column chromatography (silica gel, tetrahydrofuran). The purified oil was treated with ethereal hydrogen chloride and the resultant salt immediately recrystallized from ethyl acetate/methanol to give 3.3 g (34%) of product, mp 174°–175° C.

ANALYSIS: Calculated for $C_{21}H_{23}FN_2OS.HCl$: 61.98%C; 5.94%H; Found: 61.89%C; 5.92%H.

EXAMPLE 21

4-Cyano-1-[3-(6-fluoro-1,2-benzisoxazol-3-yl)propyl]-4-phenylpiperidine hydrochloride To 50 ml of dimethylformamide was added 4.4 g of 4-cyano-4-phenylpiperidine hydrochloride, 6.4 g of 3-(3-chloropropyl)-6-fluoro-1,2-benzisoxazole, 10 g of milled potassium carbonate, and 0.01 g of potassium iodide. After stirring at 90° C. for three hrs, the mixture was cooled, filtered, and the filtrate was evaporated to an oil. The oil was stirred with 100 ml of water for ten mins and then extracted with ether. The ether solution was washed with water (2x), saturated sodium chloride solution and dried over anhydrous magnesium sulfate. After filtering, the solvent was evaporated. The residue was filtered through a silica gel column with tetrahydrofuran. The eluant was evaporated to an oil. The oil was dissolved in ether and treated with ethereal hydrogen chloride to give 2.4 g (29%) of product, mp 235° C. (dec). Recrystallization from ethyl acetate/methanol gave the analytical sample, mp 239° C.

ANALYSIS: Calculated for $C_{22}H_{22}FN_3O\cdot HCl$: 66.07%C; 5.80%H; 10.51%N; Found: 66.20%C; 5.67%H; 10.46%N.

EXAMPLE 22

4-Acetyl-1-[3-(6-fluoro-1,2-benzisoxazol-3-yl)propyl]-4-phenylpiperidine hydrochloride To 35 ml of dimethylformamide was added 4.06 g of 4-acetyl-4-phenylpiperidine, 5.0 g of 3-(3-chloropropyl)-6-fluoro-1,2-benzisoxazole, 10 g of milled anhydrous potassium carbonate, and a few crystals of potassium iodide. After stirring at 80° C. for two hrs, the mixture was filtered. The filtrate was evaporated and the residue was stirred with 100 ml of water and then extracted into ether. The ether solution was washed with water (2x), saturated sodium chloride solution and dried over anhydrous magnesium sulfate. After filtering, the solution was acidified with ethereal hydrogen chloride and the resultant precipitate was collected and dried to yield 5.5 g (66%) of product, mp 170° C. (dec). Three recrystallizations from ethyl acetate:methanol (9:1) gave the analytical sample, mp 200°–203° C.

ANALYSIS: Calculated for $C_{23}H_{25}FN_2O_2\cdot HCl$: 66.25%C; 6.29%H; 6.72%N; Found: 65.73%C; 6.56%H; 6.50%N.

EXAMPLE 23

1-[3-(6-Fluoro-1,2-benzisoxazol-3-yl)propyl]-4-(1-hydroxyethyl)-4-phenylpiperidine hydrochloride To a mixture of 50 ml of 2-propanol and 10 ml of methanol, was added 2.8 g of 4-acetyl-1-[3-(6-fluoro-1,2-benzisoxazol-3-yl)-propyl]-4-phenylpiperidine hydrochloride and 0.76 g of sodium borohydride. After stirring at ambient temperature for twenty hrs, the mixture was evaporated. The residue was stirred with 100 ml of water for ten mins and then extracted with ether. The ether extract was washed with water (2x), saturated sodium chloride solution and dried over anhydrous magnesium sulfate. After filtering, the ether solution was acidified to pH 1 with ethereal hydrogen chloride. The resultant precipitate was collected and dried to give 2.3 g (78%) of product, mp 80° C. Recrystallization from ethyl acetate/methanol (9:1) gave the analytical sample, mp 143°–147° C.

ANALYSIS: Calculated for $C_{23}H_{27}FN_2O_2\cdot HCl$: 65.94%C; 6.69%H; 6.69%N; Found: 65.84%C; 6.91%H; 6.63%N.

EXAMPLE 24

1-[3-(6-Fluoro-1,2-benzisoxazol-3-yl)propyl]-4-(4-fluorobenzoyl)piperidine hydrochloride To 30 ml of dry dimethylformamide was added 3.4 g of 3-(3-chloropropyl)-6-fluoro-1,2-benzisoxazole, 3.1 g of 4-(4-fluorobenzoyl)piperidine, 8.0 g of sodium bicarbonate, and a crystal of potassium iodide. After stirring at 100° C. for two hrs, the mixture was filtered and the filtrate was evaporated. The residue was stirred with 100 ml of water and then extracted into ether. The ether extract was washed with water (2x), saturated sodium chloride solution and dried over anhydrous magnesium sulfate. After filtering, the ether solution was acidified with ethereal hydrogen chloride and the precipitate was collected and dried. The precipitate was recrystallized from ethyl acetate/methanol/ether to yield 3.0 g (48%) of product, mp 240°–243° C. Recrystallization from ethyl acetate/methanol/ether gave the analytical sample, mp 247°–248° C.

ANALYSIS: Calculated for $C_{22}H_{22}F_2N_2O_2\cdot HCl$: 62.78%C; 5.51%H; 6.66%; Found: 63.00%C; 5.49%H; 6.65%N.

We claim:

1. A pain alleviating composition comprising an inert pain alleviating adjuvant and, as the active ingredient, an amount effective in alleviating pain of a compound of the formula

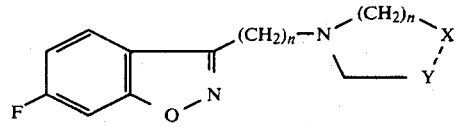

wherein X is C=O, $CR_1R_2$ wherein $R_1$ is loweralkyl, phenyl or phenylloweralkyl and $R_2$ is hydrogen, cyano, loweralkylcarbonyl, phenylcarbonyl in which the phenyl group is substituted by halogen, or a group of the formula

wherein $R_3$ is loweralkyl, $CHZR_4$ wherein Z is O or S and $R_4$ is hydrogen or phenyl substituted by trifluoromethyl or one or two halogen groups, $CHNR_5R_6$ wherein $R_5$ is hydrogen or phenyl and $R_6$ is phenylcarbonyl or loweralkylcarbonyl; X is a group of the formula

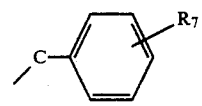

wherein $R_7$ is halogen and the dotted line represents an additional carbon to carbon bond or X and Y taken together form a phenyl nucleus; n is 1, 2 or 3; an optical antipode thereof or a pharmaceutically acceptable acid addition salt thereof.

2. A method of alleviating pain comprising administering to a mammal in need of pain alleviation, a pain alleviating effective amount of a compound of the formula

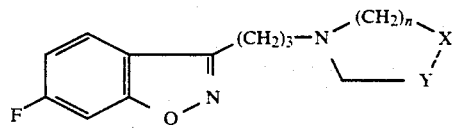

wherein X is C=O, $CR_1R_2$ wherein $R_1$ is loweralkyl, phenyl or phenylloweralkyl and $R_2$ is hydrogen, cyano, loweralkylcarbonyl, phenylcarbonyl in which the phenyl group is substituted by halogen, or a group of the formula

wherein $R_3$ is loweralkyl, $CHZR_4$ wherein Z is O or S and $R_4$ is hydrogen or phenyl substituted by trifluoromethyl or one or two halogen groups, $CHNR_5R_6$ wherein R₅ is hydrogen or phenyl and R₆ is phenylcarbonyl or loweralkylcarbonyl; X is a group of the formula

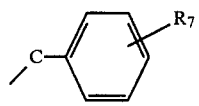

wherein R₇ is halogen and the dotted line represents an additional carbon to carbon bond or X and Y taken together form a phenyl nucleus; n is 1, 2 or 3; an optical antipode thereof or a pharmaceutically acceptable acid additional salt thereof.

3. A blood pressure reducing composition comprising an inert blood pressure reducing adjuvant and, as the active ingredient, an amount effective in reducing blood pressure of a compound of the formula

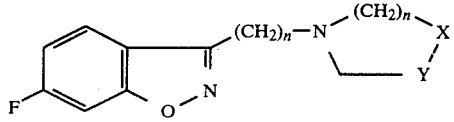

wherein X is C=O, CR₁R₂ wherein R₁ is loweralkyl, phenyl or phenylloweralkyl and R₂ is hydrogen, cyano, loweralkylcarbonyl, phenylcarbonyl in which the phenyl group is substituted by halogen, or a group of the formula

wherein R₃ is loweralkyl, CHZR₄ wherein Z is O or S and R₄ is hydrogen or phenyl substituted by trifluoromethyl or one or two halogen groups, CHNR₅R₆ wherein R₅ is hydrogen or phenyl and R₆ is phenylcarbonyl or loweralkylcarbonyl; X is a group of the formula

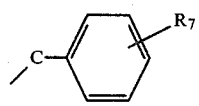

wherein R₇ is halogen and the dotted line represents and additional carbon to carbon bond or X and Y taken together form a phenyl nucleus; n is 1, 2 or 3; an optical antipode thereof or a pharmaceutically acceptable acid additional salt thereof.

4. A method of reducing blood pressure comprising administering to a mammal in need of blood pressure reduction a blood pressure reducing effective amount of a compound of the formula

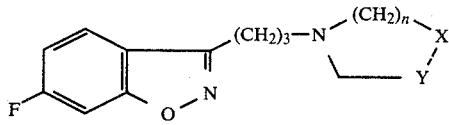

wherein X is C=O, CR₁R₂ wherein R₁ is loweralkyl, phenyl or phenylloweralkyl and R₂ is hydrogen, cyano, loweralkylcarbonyl, phenylcarbonyl in which the phenyl group is substituted by halogen, or a group of the formula

wherein R₃ is loweralkyl, CHZR₄ wherein Z is O or S and R₄ is hydrogen or phenyl substituted by trifluoromethyl or one or two halogen groups, CHNR₅R₆ wherein R₅ is hydrogen or phenyl and R₆ is phenylcarbonyl or loweralkylcarbonyl; X is a group of the formula

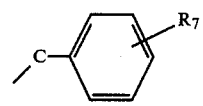

wherein R₇ is halogen and the dotted line represents an additional carbon to carbon bond or X and Y taken together form a phenyl nucleus; n is 1, 2 or 3; an optical antipode thereof or a pharmaceutically acceptable acid additional salt thereof.

5. A psychoses treating composition comprising an inert psychoses treating adjuvant and, as the active ingredient, an amount effective in treating psychoses of a compound of the formula

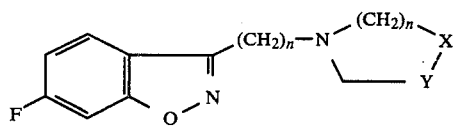

wherein X is C=O, CR₁R₂ wherein R₁ is hydrogen, loweralkyl, phenyl or phenylloweralkyl and R₂ is hydrogen, cyano, loweralkylcarbonyl, phenylcarbonyl in which the phenyl group is substituted by halogen, or a group of the formula

wherein R₃ is loweralkyl, CHZR₄ wherein Z is O or S and R₄ is hydrogen or phenyl substituted by trifluoromethyl or one or two halogen groups, CHNR₅R₆ wherein R₅ is hydrogen or phenyl and R₆ is phenylcarbonyl or loweralkylcarbonyl; X is a group of the formula

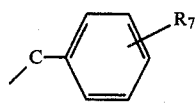

wherein R₇ is halogen and the dotted line represents an additional carbon to carbon bond or X and Y taken together form a phenyl nucleus; n is 1, 2 or 3; an optical antipode thereof or a pharmaceutically acceptable acid additional salt thereof.

6. A method of treating psychoses comprising administering to a mammal in need of psychoses treatment a psychoses treating effective amount of a compound of the formula

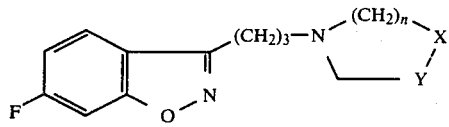

wherein X is C=O, CR₁R₂ wherein R₁ is loweralkyl, phenyl or phenylloweralkyl and R₂ is hydrogen, cyano, loweralkylcarbonyl, phenylcarbonyl in which the phenyl group is substituted by halogen, or a group of the formula

wherein $R_3$ is loweralkyl, $CHZR_4$ wherein Z is O or S and $R_4$ is hydrogen or phenyl substituted by trifluoromethyl or one or two halogen groups, $CHNR_5R_6$ wherein $R_5$ is hydrogen or phenyl and $R_6$ is phenylcarbonyl or loweralkylcarbonyl; X is a group of the formula

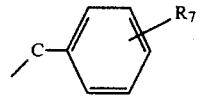

wherein $R_7$ is halogen and the dotted line represents an additional carbon to carbon bond or X and Y taken together form a phenyl nucleus; n is 1, 2 or 3; an optical antipode thereof or a pharmaceutically acceptable acid additional salt thereof.

* * * * *